(12) United States Patent
Sanders

(10) Patent No.: US 10,206,692 B2
(45) Date of Patent: Feb. 19, 2019

(54) OSTEOTOMY GUIDE AND METHOD OF USING THE SAME

(71) Applicant: Mark Sanders, Houston, TX (US)

(72) Inventor: Mark Sanders, Houston, TX (US)

(*) Notice: Subject to any disclaimer, the term of this patent is extended or adjusted under 35 U.S.C. 154(b) by 335 days.

(21) Appl. No.: 15/015,473

(22) Filed: Feb. 4, 2016

(65) Prior Publication Data

US 2016/0270800 A1 Sep. 22, 2016

Related U.S. Application Data

(60) Provisional application No. 62/111,742, filed on Feb. 4, 2015.

(51) Int. Cl.
| A61B 17/17 | (2006.01) |
| A61B 17/88 | (2006.01) |
| A61B 17/56 | (2006.01) |
| A61B 17/90 | (2006.01) |

(52) U.S. Cl.
CPC .......... *A61B 17/17* (2013.01); *A61B 17/8897* (2013.01); *A61B 2017/565* (2013.01); *A61B 2017/90* (2013.01)

(58) Field of Classification Search
CPC ................ A61B 17/17; A61B 2017/90; A61B 2017/565
See application file for complete search history.

(56) References Cited

U.S. PATENT DOCUMENTS

| 4,335,715 A | 6/1982 | Kirkley |
| 4,421,112 A * | 12/1983 | Mains ................. A61B 17/152 606/75 |
| 4,565,191 A | 1/1986 | Slocum |
| 5,246,444 A | 9/1993 | Schreiber |
| 5,254,119 A | 10/1993 | Schreiber |
| 5,324,295 A * | 6/1994 | Shapiro ............. A61B 17/1714 606/86 R |
| 5,417,694 A | 5/1995 | Marik et al. |
| 5,449,360 A * | 9/1995 | Schreiber ............. A61B 17/15 606/87 |
| 7,172,596 B2 | 2/2007 | Coon et al. |
| 2007/0265634 A1 | 11/2007 | Weinstein |
| 2008/0015603 A1 | 1/2008 | Collazo |
| 2016/0166350 A1* | 6/2016 | Burkhardt .......... A61B 17/1615 206/572 |

\* cited by examiner

*Primary Examiner* — Olivia C Chang

(74) *Attorney, Agent, or Firm* — Michael E. Dockins; Shumaker, Loop & Kendrick, LLP

(57) ABSTRACT

Osteotomy tools and procedures are provided that include a sets of guides in which pins are placed through conduits in the guides with a close tolerance and into the bone at predetermined angles. One pin is placed at a correction angle subtending from one of a pair of parallel pins placed across an osteotomy site. After the osteotomy is completed, a bone correction is achieved by rotating the pin at the correction angle to be parallel to the one of the parallel pins located across the osteotomy site. A parallel pin guide is placed over these two pins to maintain the bone correction and stabilize the osteotomy, allowing fixation of the corrected bone segments.

12 Claims, 9 Drawing Sheets

OSTEOTOMY GUIDE AND METHOD OF USING THE SAME

CROSS-REFERENCE TO RELATED APPLICATIONS

This application claims the benefit of U.S. Provisional Application No. 62/111,742, filed on Feb. 4, 2015. The entire disclosure of the above application is incorporated herein by reference.

FIELD

The present technology relates to systems and methods employed during an osteotomy, including ways to maintain and stabilize intraoperative bone corrections.

INTRODUCTION

This section provides background information related to the present disclosure which is not necessarily prior art.

An osteotomy includes a surgical division or sectioning of bone. The procedure can include a surgical operation whereby a bone is cut to shorten, lengthen, or change its alignment. Various osteotomy procedures are used to correct various bone defects and abnormalities, including deformities of the appendages, such as metatarsal deviations (e.g., a hallux valgus), or to straighten a bone that has healed at an undesirable configuration or angle following a fracture. Other uses include corrections of the hip, knee, or limb (e.g., coxa vara, genu valgum, and genu varum). An osteotomy can also be performed to relieve pain in arthritis, including arthritis of the hip and knee.

In certain cases, a bone can be incorrectly formed, as twisted or rotated along its longitudinal axis or having an angular deformity therein. An osteotomy of the deformity can sever the bone and reconnect one or more segments in proper orientation with respect to each other. In the instance of a rotational deformity, the correcting procedure can include the steps of severing the bone into multiple segments and twisting or rotating the segments with respect to each other, and then connecting the segments back together in a correct or preferred alignment. Where a bone has an improper angle formed therein, the correcting procedure can include the steps of severing the bone in one or more locations on opposite sides of the angle in the bone to form a small wedge shaped segment of bone that has the same angle as the deformity of the bone, removing the wedge of bone, and reorienting the remaining segments in alignment and connecting the segments together.

While it can be a simple matter to perceive the desired angle of correction for a malformed bone or a bone defect, an orthopedic surgeon often must cut through the bone and adjust the bone segments with respect to each other to correct the deformity. The correction procedure can be complicated by difficulties in correctly aligning and maintaining alignment of the bone segments during the operation. For example, if the bone is to be rotated, it can be difficult to perceive the exact angle through which the bone is rotated, and it can also be difficult to maintain the proper angle of rotation during the reconnection procedure for each of the one or more bone segments.

SUMMARY

The present technology includes systems, processes, and articles of manufacture that relate to performing an osteotomy. In particular, a system according to the present technology includes a guide or a series of guides in which pins are placed through holes in the guides with a close tolerance, and then into a bone at pre-measured angles. After the osteotomy is completed, a correction is achieved by rotating one pin to be parallel to the other, and a parallel guide is placed over the two pins, which assures the correction, and provisionally stabilizes the osteotomy such that a surgeon's attention can be directed toward a remainder of the internal fixation procedure.

In certain embodiments, a set of guides for use in an osteotomy is provided that includes a parallel guide and an angled guide. The parallel guide has a first conduit passing therethrough and a second conduit passing therethrough, where the first conduit and the second conduit are substantially parallel. The angled guide has a first angled conduit passing therethrough and a second angled conduit passing therethrough, where the first angled conduit and the second angled conduit are arranged at a predetermined angle. The set of guides can also include a plurality of angled guides, where each angled guide has a first angled conduit passing therethrough and a second angled conduit passing therethrough. The first angled conduit and the second angled conduit of each guide are arranged at a predetermined angle, where the predetermined angle of each angled guide is different. The set of guides can further include one or more pins configured to fit within the first, second, and angled conduits.

Methods of correcting a defect in a bone are also provided that include placing a first pin into the bone on a first side of an osteotomy site and placing a second pin into the bone on a second side of the osteotomy site, the first pin and the second pin being substantially parallel. A correction pin is placed into the bone at a correction angle relative to the second pin. An osteotomy is performed at the osteotomy site. A portion of the bone including one of the first pin and the correction pin is rotated so that the first pin and the correction pin are substantially parallel.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A depicts a longitudinal, cross-sectional view and FIG. 1B depicts an end view taken from line 1B in FIG. 1A.

FIG. 2A depicts a side view and FIG. 2B depicts an end view taken from line 2B in FIG. 2A.

FIG. 3A depicts a side view and FIG. 3B depicts an end view taken from line 3B in FIG. 3A.

FIG. 4A depicts a side view and FIG. 4B depicts an end view taken from line 4B in FIG. 4A.

Figure 5A:
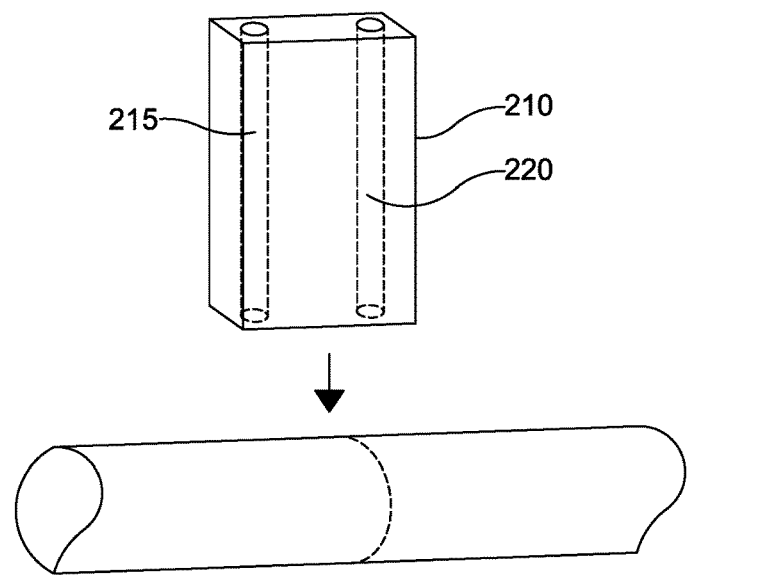
Figure 5B:
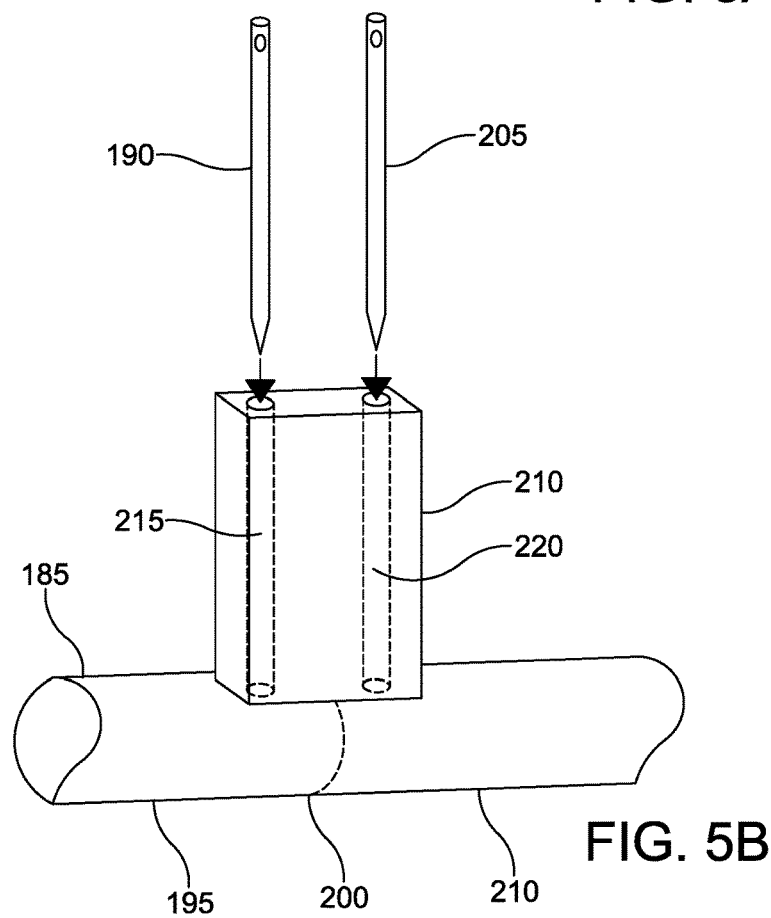
Figure 5C:
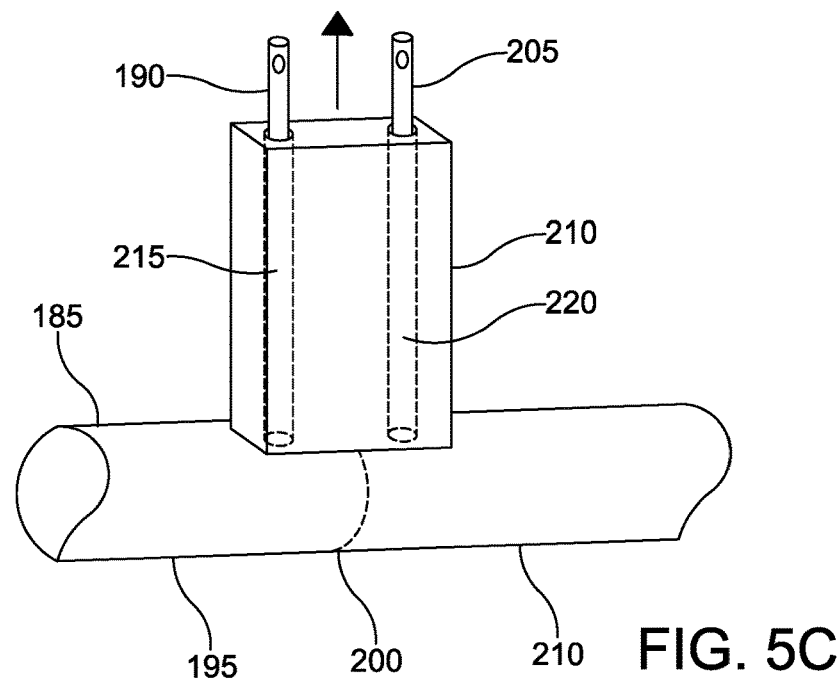
Figure 5D:
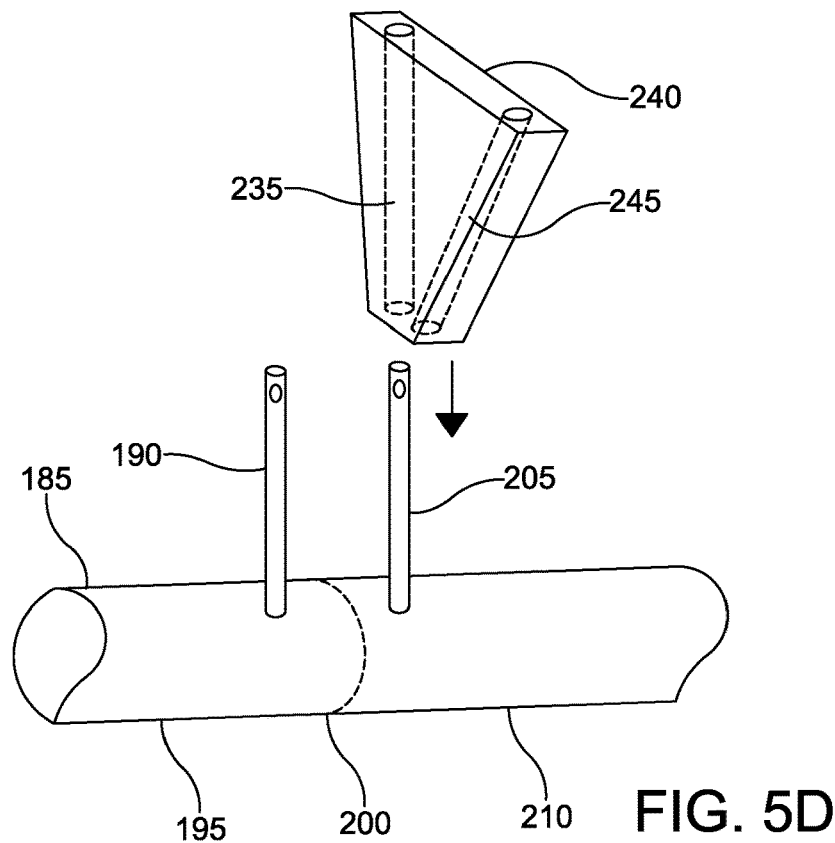
Figure 5E:
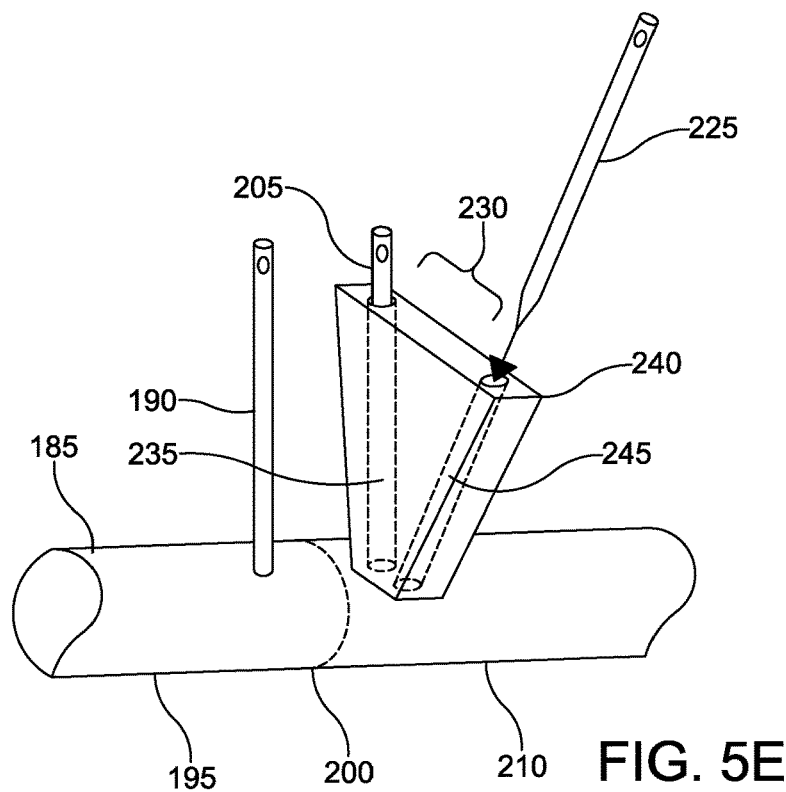
Figure 5F:
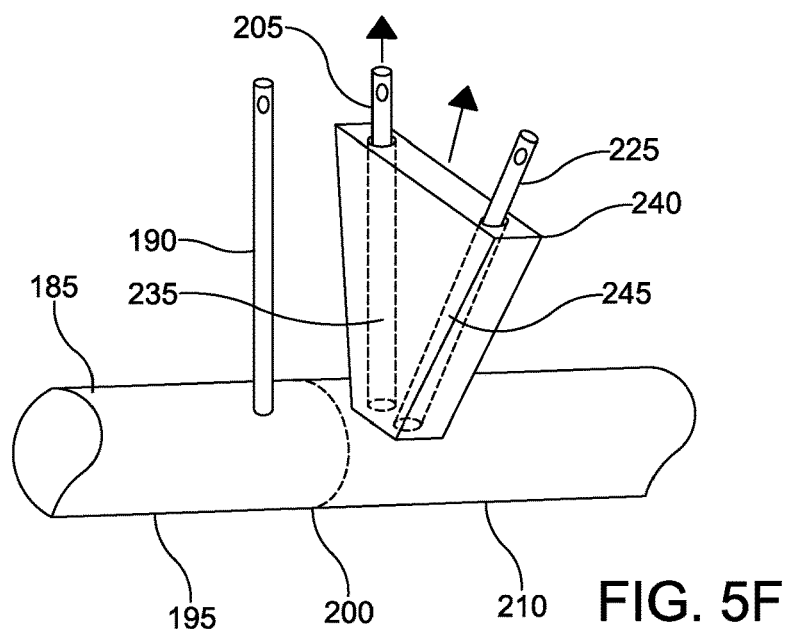
Figure 5G:
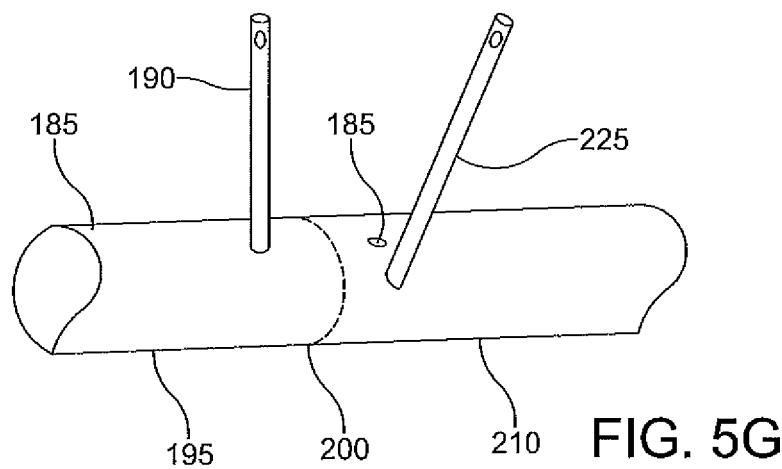
Figure 5H:
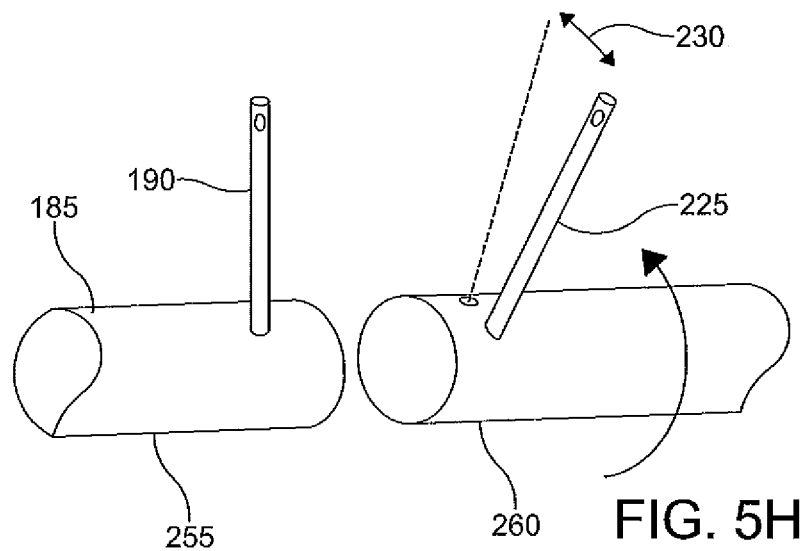
Figure 5I:
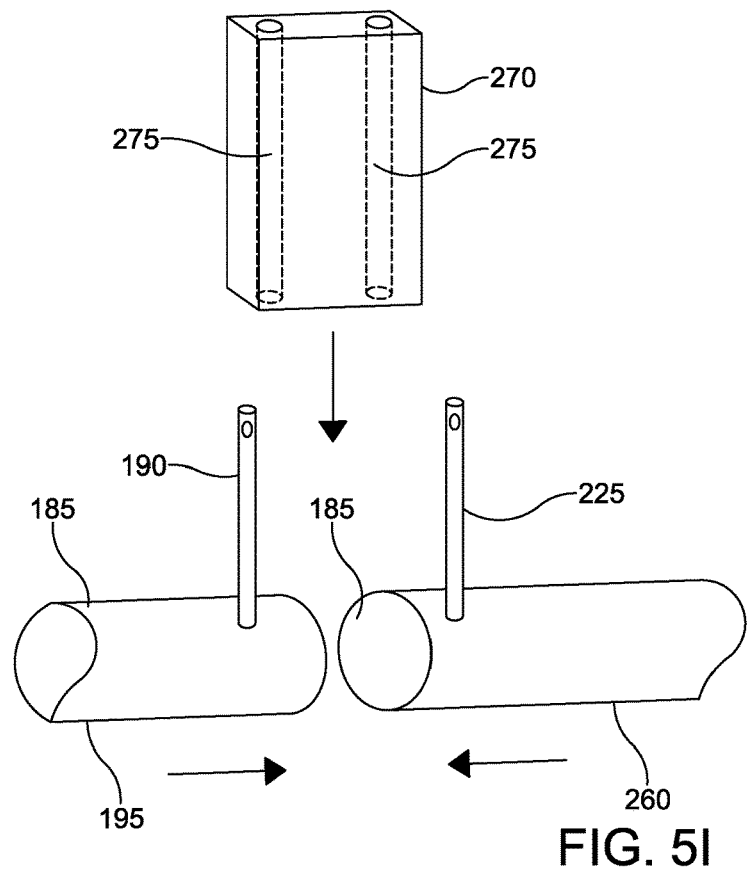
Figure 5J:
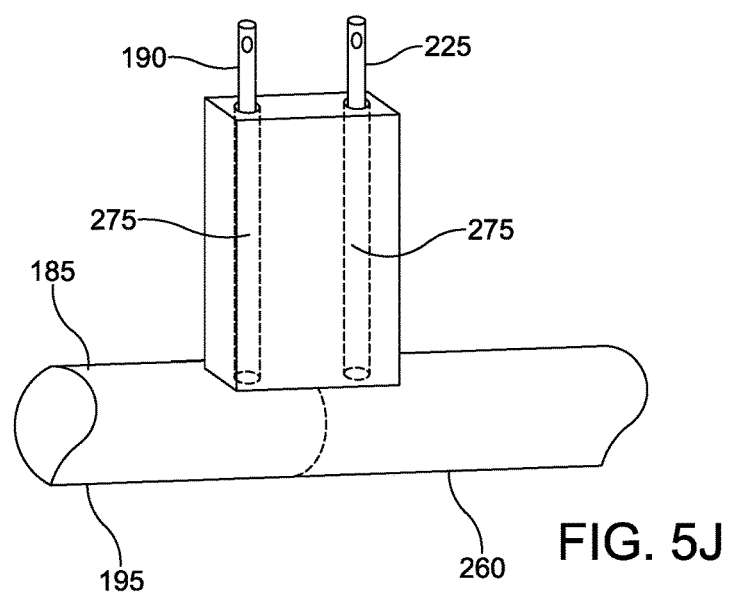

FIGS. 5A-J illustrate an embodiment of a method of correcting a defect in a bone according to the present technology, where FIG. 5A depicts a parallel guide being placed across an osteotomy site on a bone, FIG. 5B depicts first and second pins disposed through conduits in the parallel guide and into the bone, FIG. 5C depicts removal of the parallel guide, FIG. 5D depicts the second pin being disposed through a first angled conduit passing through an angled guide, FIG. 5E depicts a correction pin being placed through a second angled conduit of the angled guide and into the bone, FIG. 5F depicts the second pin and the angled guide being removed, FIG. 5G depicts the remaining first pin and correction pin across the osteotomy site, FIG. 5H depicts an osteotomy at the osteotomy site, where the bone is cut into a first bone segment including the first pin and a second bone segment including the correction pin, and the second bone segment including the correction pin is rotated so that the correction pin and the first pin are substantially parallel, FIG. 5I depicts the first pin held substantially parallel with the correction pin using a parallel guide, and FIG. 5J depicts the first pin and the correction pin held substantially parallel using a parallel guide so that the bone can be fixed across the osteotomy site.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" and all geometric and spatial descriptors are to be understood as modified by the word "substantially" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components, or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology relates to osteotomy procedures, including methods, systems, and articles of manufacture employed in such procedures. In particular, increasing orthopedic surgical attention is being directed to disorders of bone alignment in the lower extremities. Although such disorders have long been part of orthopedic surgery, they have become somewhat deemphasized as other procedures, such as arthroscopic and minimally invasive procedures, have become more popular. However, maintenance and correction of bone alignment via osteotomy continues to provide an important means to address orthopedic issues in the lower extremities, and in certain cases, has reemerged as a preferred means to address bone alignment issues.

Alignment occurs in three planes, including three analogous translations. The planes include the frontal or coronal plane, the side view or sagittal plane, and the transverse or rotational plane. Analogous translational movements occur perpendicular to the plane. For the frontal plane, these include those in which the distal (closer to the foot) fragment moves either medially (to the body center) or lateral (to the outside of the body). For the sagittal plane, these translations include movements anterior or posterior. For the transverse plane, these movements include lengthening or shortening of the limb.

A common adage in orthopedic surgery is that measurements are made with a micrometer (using radiography), marked with a crayon (on an X-ray film), and (the bone) cut with an axe. Deformity corrections, for example, can commonly occur within a range of several degrees greater or lesser than the ideal correction. This has been the case for a long time, and is a likely reason why some orthopedic surgeons may avoid complicated cases. The advent of digital osteotomy, planning, as well as increased expectation on the part of physicians and patients, has demanded improvements in the accuracy of correction.

A typical correction intra-operative measurement can include the placement of a first pin into the bone, below the expected location of correction, and a second pin above the location of correction at an angle, utilizing a goniometer or a protractor. Placement of the second pin can be done by trying to mimic the angle set by the goniometer. For example, a surgeon places the second pin, and while an assistant is holding the bone and the instrument, the surgeon steps away from the operative field to determine whether or not the pin is parallel to the instrument, and the other limb of the instrument is parallel to the first pin. The technology presented herein provides a better solution to perform and maintain measurements during an osteotomy procedure.

To this end, the present technology improves the accuracy of correction, including the accuracy required for rotational corrections. The present technology employs an angled guide or a series of angled guides, in which pins are placed through angled conduits in the angled guide with a close tolerance, and then into the bone at pre-measured angles. After the osteotomy is completed, the correction is achieved by rotating one pin to be parallel to the other pin, and a parallel guide is placed over the two pins, which assures the desired correction, and provisionally stabilizes the osteotomy such that the surgeon's attention can be directed toward the internal fixation.

Aspects of the present technology include a parallel guide and one or more various angled guides. A number of different guides can be constructed, including different sized and shaped parallel guides and angled guides, where the parallel guides have parallel conduits therethrough and the angled guides have angled conduits therethrough arranged at predetermined angles, such as angles between 2° and 25°. Other examples of guides include a 0° or parallel guide and one or more angled guides having angled conduits at predetermined angles of 2°, 4°, 6°, 8°, 10°, 15°, 20°, and 25°. The parallel guide can have a rectangular cross-section taken along a longitudinal axis and the angled guides can have a trapezoidal cross-section taken along a longitudinal axis. The non-parallel edges of the trapezoidal shaped angled guide can follow the angled conduits within the angled guide and thereby present the same predetermined angle. Other guides of various degrees intermediate of these examples, or guides having smaller or greater angles than these examples are possible. The guides can be provided as a set, where the set includes a parallel guide and one or more angled guides. The parallel guide can have a first conduit passing therethrough and a second conduit passing therethrough, where the first conduit and the second conduit are substantially parallel. Each angled guide can have a first angled conduit passing therethrough and a second angled conduit passing therethrough, where the first angled conduit and the second angled conduit are arranged at a predetermined angle. The predetermined angle of each angled guide in the set of guides can be different. Each angled guide can be marked with an indicia representing the predetermined angle of the respective angled guide; e.g., "10" where the first angled conduit and the second angled conduit are arranged at a 10° angle. The various conduits of the guides can each be configured to receive a pin and the set of guides can further include a plurality of pins.

Various ways of performing an osteotomy using such guides are possible. In certain embodiments, the guides can be used to correct a defect in a bone as follows. The skin and soft tissues are divided, and the bone is exposed in the region where the correction is set to occur. A first pin is placed into the bone on a first side of an osteotomy site and a second pin is placed into the bone on a second side of the osteotomy site, where the first pin and the second pin are substantially parallel. A correction pin is placed into the bone at a correction angle relative to the second pin. An osteotomy is performed at the osteotomy site. A portion of the bone including one of the first pin and the correction pin is rotated so that the first pin and the correction pin are substantially parallel.

For example, utilizing a parallel guide, two parallel pins (e.g., ⅛ inch diameter) are placed in the bone above and below the site of the proposed osteotomy site. The parallel guide is removed and an angled guide with a desired built-in correction is placed over one of the pins. In correcting a bone defect of the lower extremities, the parallel guide can be placed over a pin closest to the foot, but it can be done either way. A pin can be drilled into the bone at a predetermined angle. The angled guide is removed as is the parallel pin on that side. This leaves one pin above the osteotomy site, and another pin below the osteotomy site, subtending the predetermined angle. Thus, the present technology provides accurate correction without the use of a robot, a computer, or any other high tech, high cost equipment, beyond the occasional X-ray.

The angled guides can also be used in conjunction with each other and in a sequential fashion. For example, in the event that a correction of 22° is necessary, following the placement of a 20° angled guide, and removal of the parallel pin, a 2° angled guide is placed and a pin which subtends a 2° angle with the 20° angled pin is placed in the bone. The 20° angled guide can then be removed, leaving an additive angle of correction of 22°. Conversely, a pin placed using the 20° angled guide can be modified by reducing the angle of correction; e.g., a 20° angle can be reduced to 18° by subtraction with the 2° angled guide. As such, with an inventory of various guides, accuracy in the degree of correction can be achieved using a limited set of guides without requiring individual guides for every possible angle of correction.

The osteotomy can be performed with a power saw or an osteotome (chisel), and the distal (toward the foot) fragment can be rotated into parallelism with the proximal fragment. This position can be confirmed and held stably by the placement of the parallel guide over the two remaining pins, such that the surgeon and any assistant(s) can busy themselves with the internal fixation, rather than holding the fragments together.

Not infrequently, the orthopedic surgeon can be faced with a deformity that requires an angular correction in the frontal or sagittal plane by removing a wedge of bone, known in the orthopedic vernacular as a closing wedge osteotomy. The angled guides provided herein can each be configured to have a substantially trapezoidal cross-section taken substantially orthogonal to a longitudinal axis of the angled guide. The non-parallel edges of the angled guide can therefore match and subtend the respective angle of the angled conduits therein. In particular, an angled guide can be placed strategically on the bone surface and pinned in place through one or more orthogonal conduits that pass through the angled guide in a direction substantially orthogonal to the longitudinal axis of the angled guide. The orthogonal conduit(s) can be ⅛ inch (2.8 mm) in diameter, for example. The non-parallel trapezoidal angled guide edges can then be utilized as guides for the power saw or osteotome. In doing so, an accurate wedge, either triangular or trapezoidal, can be removed from the bone to insure an accurate correction of the bone deformity.

Figure 1A:
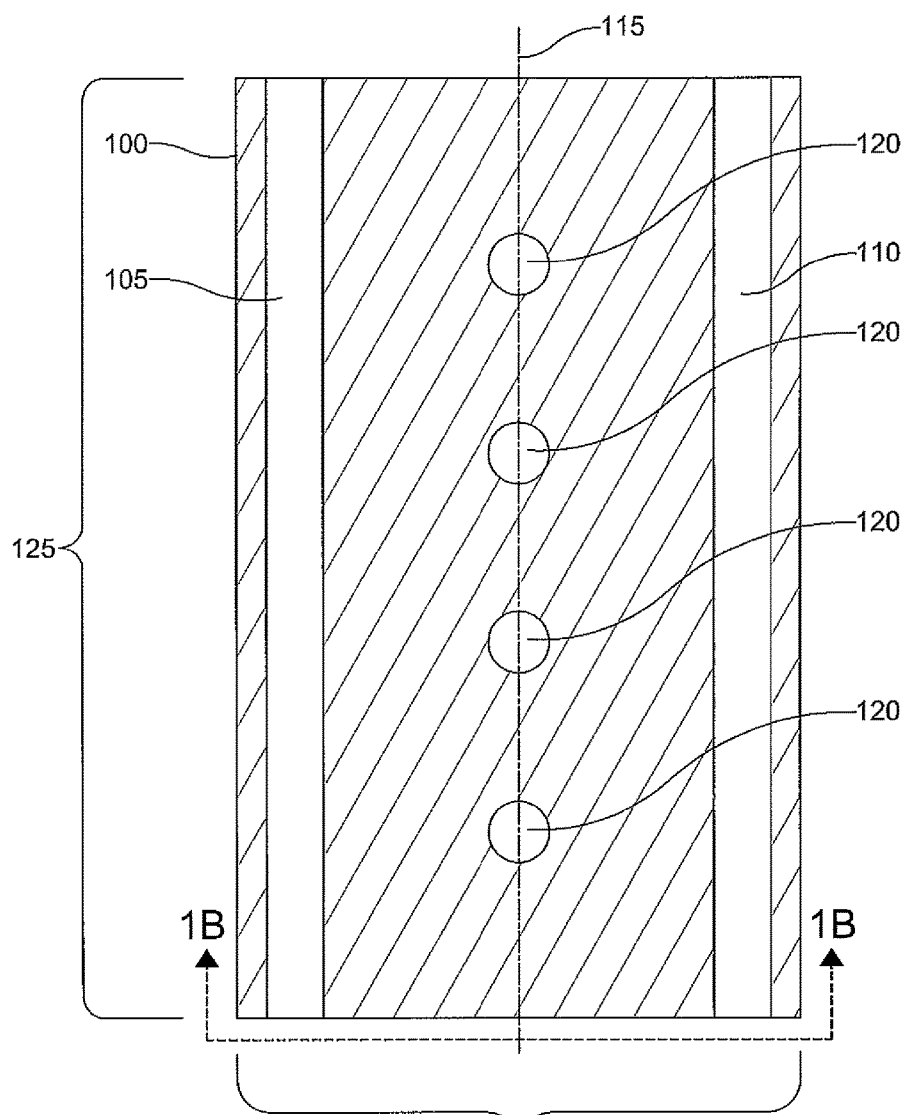
FIGS. 1A & 1B show an embodiment of a parallel guide according to the present technology, where
Figure 1B:
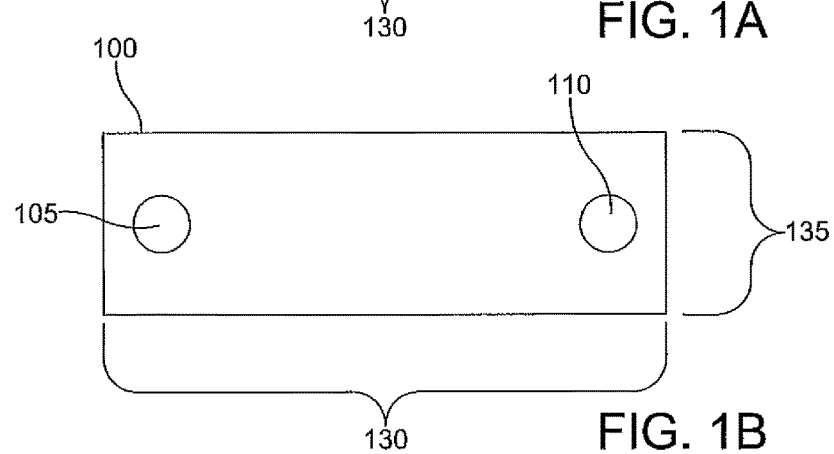

With particular reference to FIGS. 1-4, example embodiments of guides for use in an osteotomy are shown. A parallel guide 100 is shown in FIG. 1, where the parallel guide 100 includes a first conduit 105 passing therethrough and a second conduit 110 passing therethrough. The first conduit 105 and the second conduit 110 are substantially parallel. As shown, the parallel guide 100 has a substantially rectangular cross-section taken substantially orthogonal to a longitudinal axis 115. Four orthogonal conduits 120 pass through the parallel guide 100 in a direction substantially orthogonal to the longitudinal axis 115 and are disposed between the first conduit 105 and the second conduit 110. However, the parallel guide 100 can have a single orthogonal conduit 120 or a plurality of orthogonal conduits 120. The orthogonal conduits 120 can be aligned with the longitudinal axis 115, as shown, and/or can be positioned elsewhere on the parallel guide 100. The parallel guide 100 can have various dimensions, including a height 125 of about 2.5 cm to about 7.5 cm, a length 130 of about 1.5 cm to about 4.5 cm, and a width 135 of about 0.5 cm to about 1.5 cm. As one example, the parallel guide 100 can have a height 125 of about 5 cm, a length of about 3 cm, and a width of about 1 cm.

Figure 2A:
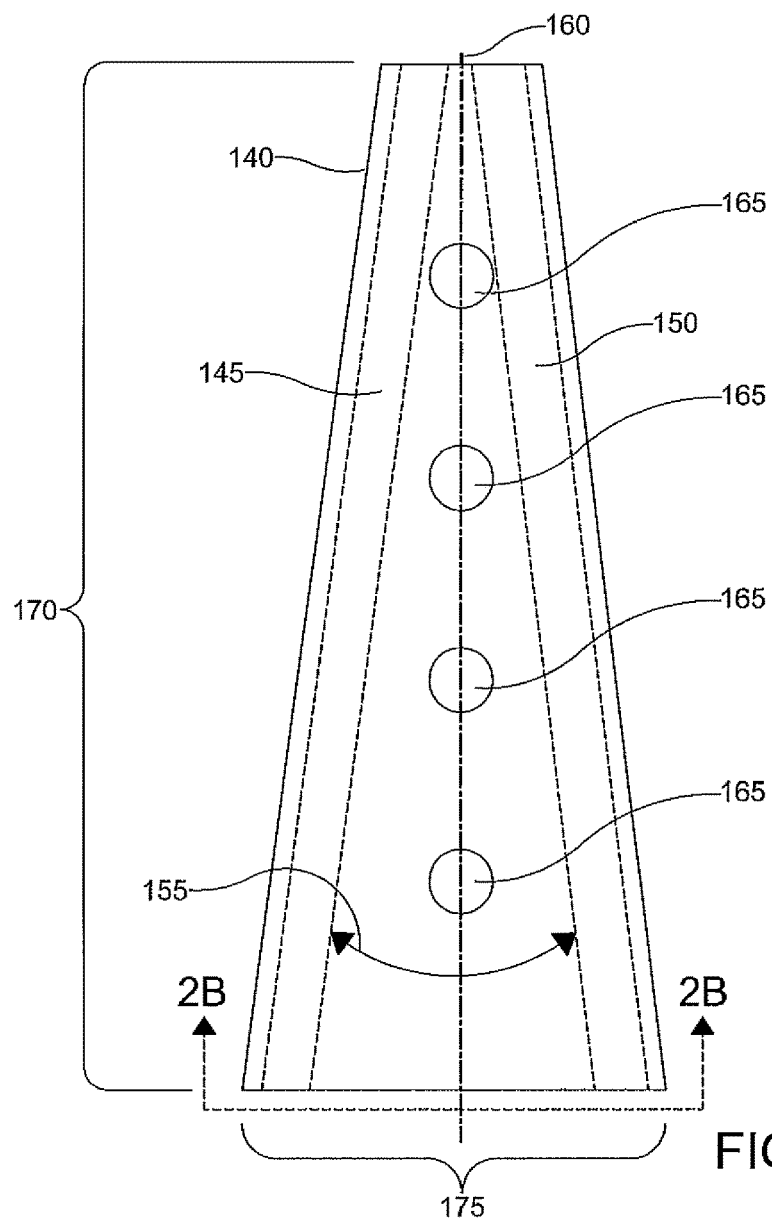
FIGS. 2A & 2B show an embodiment of an angled guide according to the present technology, where
Figure 2B:
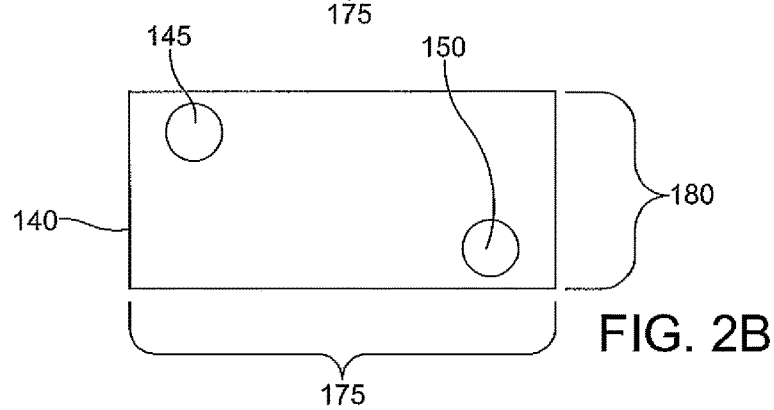
Figure 3A:
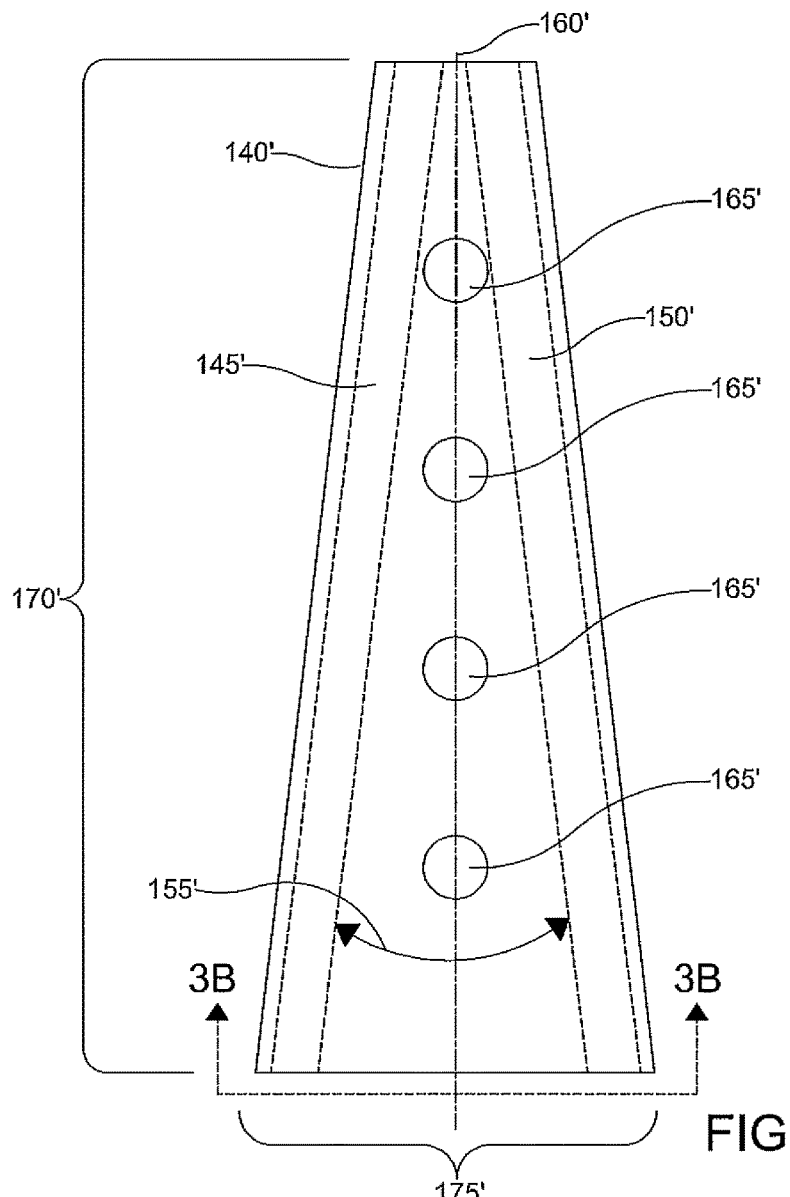
FIGS. 3A & 3B show another second embodiment of an angled guide according to the present technology, where
Figure 3B:
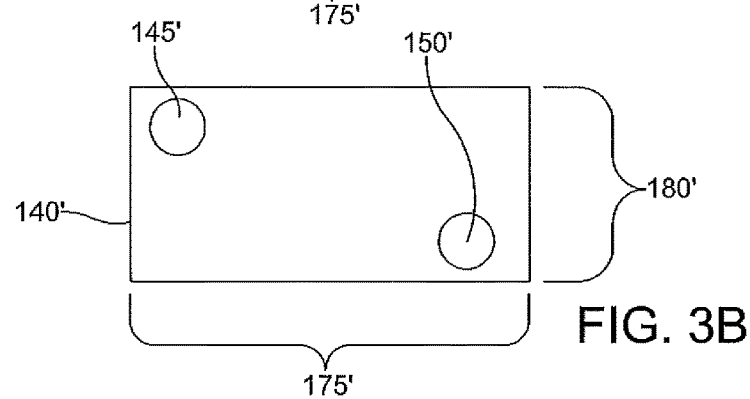
Figure 4A:
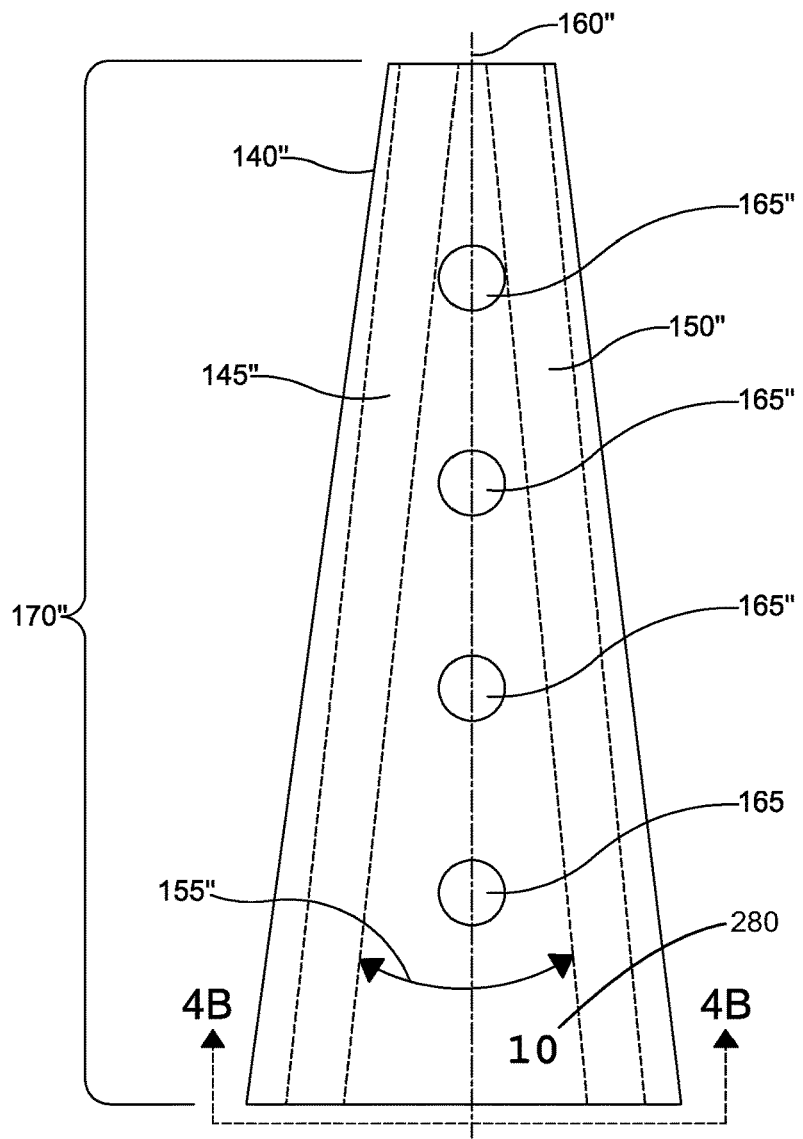
FIGS. 4A & 4B show yet another embodiment of an angled guide according to the present technology, where
Figure 4B:
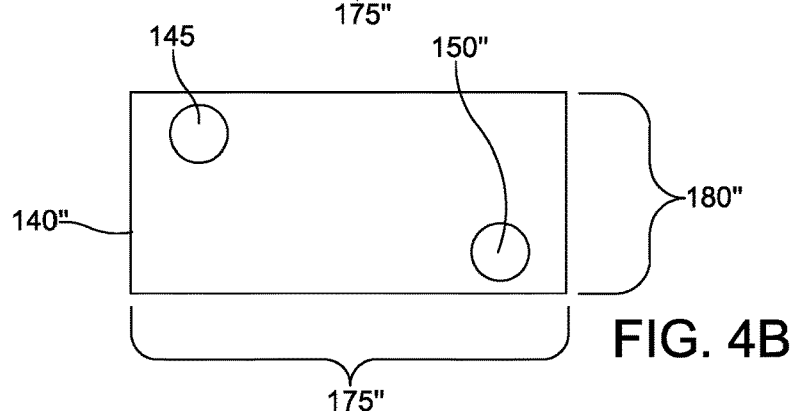

Three embodiments of angled guides 140, 140', 140" are shown in FIGS. 2-4, where like features are indicated with like reference numerals followed by a prime (') or double prime (") designation in successive figures. A first embodiment of an angled guide 140 is shown in FIG. 2 where the angled guide 140 includes a first angled conduit 145 passing therethrough and a second angled conduit 150 passing therethrough. The first angled conduit 145 and the second angled conduit 150 are arranged at a predetermined angle 155. For example, the predetermined angle 155 can be 12.5°. As shown, the angled guide 140 has a substantially trapezoidal cross-section taken substantially orthogonal to a longitudinal axis 160. Four orthogonal conduits 165 pass through the angled guide 140 in a direction substantially orthogonal to a longitudinal axis 160 and are disposed between the first angled conduit 145 and the second angled conduit 150. However, the angled guide 140 can have a single orthogonal conduit 165 or a plurality of orthogonal conduits 165. The orthogonal conduits 165 can be aligned with the longitudinal axis 160, as shown, and/or can be positioned elsewhere on the angled guide 140. The angled guide 140 can have various dimensions and can be configured with various predetermined angles 155, including a height 170 of about 2.5 cm to about 7.5 cm, a length 175 of about 1.5 cm to about 4.5 cm, and a width 180 of about 0.5 cm to about 1.5 cm. As one example, the angled guide 140 can have a height 170 of about 5.1 cm, a length 175 of about 2.9 cm, and a width 180 of about 1 cm.

A second embodiment of an angled guide 140' is shown in FIG. 3 where the angled guide 140' includes a first angled conduit 145' passing therethrough and a second angled conduit 150' passing therethrough. The first angled conduit 145' and the second angled conduit 150' are arranged at a predetermined angle 155'. For example, the predetermined angle 155' can be 7.5°. As shown, the angled guide 140' has a substantially trapezoidal cross-section taken substantially orthogonal to a longitudinal axis 160'. Four orthogonal conduits 165' pass through the angled guide 140' in a direction substantially orthogonal to a longitudinal axis 160' and are disposed between the first angled conduit 145' and the second angled conduit 150'. However, the angled guide 140' can have a single orthogonal conduit 165' or a plurality of orthogonal conduits 165'. The orthogonal conduits 165' can be aligned with the longitudinal axis 160', as shown, and/or can be positioned elsewhere on the angled guide 140'. The angled guide 140' can have various dimensions and can be configured with various predetermined angles 155', including a height 170' of about 2.5 cm to about 7.5 cm, a length 175' of about 1.5 cm to about 4.5 cm, and a width 180' of about 0.5 cm to about 1.5 cm. As one example, the angled guide 140' can have a height 170' of about 5.1 cm, a length 175' of about 2.2 cm, and a width 180' of about 1 cm.

A third embodiment of an angled guide 140" is shown in FIG. 4 where the angled guide 140" includes a first angled conduit 145" passing therethrough and a second angled conduit 150" passing therethrough. The first angled conduit 145" and the second angled conduit 150" are arranged at a predetermined angle 155". For example, the predetermined angle 155" can be 10°. The predetermined angle 155" can be identified by an indicia 280 (e.g., "10") marked on the angled guide 140". As shown, the angled guide 140" has a substantially trapezoidal cross-section taken substantially orthogonal to a longitudinal axis 160". Four orthogonal conduits 165" pass through the angled guide 140" in a direction substantially orthogonal to a longitudinal axis 160" and are disposed between the first angled conduit 145" and the second angled conduit 150". However, the angled guide 140" can have a single orthogonal conduit 165" or a plurality of orthogonal conduits 165". The orthogonal conduits 165" can be aligned with the longitudinal axis 160", as shown, and/or can be positioned elsewhere on the angled guide 140". The angled guide 140" can have various dimensions and can be configured with various predetermined angles 155", including a height 170" of about 2.5 cm to about 7.5 cm, a length 175" of about 1.5 cm to about 4.5 cm, and a width 180" of about 0.5 cm to about 1.5 cm. As one example, the angled guide 140" can have a height 170" of about 5.1 cm, a length 175" of about 2.5 cm, and a width 180' of about 1 cm.

With particular reference to FIGS. 5A-J, an example embodiment of a method for correcting a defect in a bone 185 is illustrated. A first pin 190 is placed into the bone 185 on a first side 195 of an osteotomy site 200 and a second pin 205 is placed into the bone 185 on a second side 210 of the osteotomy site 200, where the first pin 190 and the second pin 205 are substantially parallel. In particular, FIG. 5A shows a parallel guide 210 being placed across the osteotomy site 200 on the bone 185. The parallel guide 210 has a first conduit 215 passing therethrough to the first side 195 of the osteotomy site 200 and a second conduit 220 passing therethrough to the second side 210 of the osteotomy site 200, where the first conduit 215 and the second conduit 220 are substantially parallel. FIG. 5B shows the first pin 190 being disposed through the first conduit 215 and into the bone 185 and the second pin 205 being disposed through the second conduit 220 and into the bone 185. FIG. 5C shows the parallel guide 210 being removed to leave the first pin 190 and the second pin 205 in the bone 185.

A correction pin 225 is placed into the bone 185 at a correction angle 230 relative to the second pin 205, as shown in FIGS. 5D-G. In particular, FIG. 5D shows the second pin 205 being disposed through a first angled conduit 235 passing through an angled guide 240. The angled guide 240 includes a second angled conduit 245 passing therethrough for receiving the correction pin 225, where the first angled conduit 235 and the second angled conduit 245 subtend the correction angle 230. FIG. 5E shows the correction pin 225 being placed through the second angled conduit 245 of the angled guide 240 and into the bone 185 and FIG. 5F shows the second pin 205 and the angled guide 240 being removed. FIG. 5G shows the remaining first pin 190 and correction pin 225 across the osteotomy site 200, including the former location 250 of the second pin 205.

It should be noted that one or more additional angled guides (not shown) can be used to modify the final location of a correction pin and a correction angle. The use of one or more additional guides is not depicted in FIGS. 5A-J, but can be readily understood from the following description. The second pin is disposed through a first angled conduit passing through a first angled guide, where the first angled guide has a second angled conduit passing therethrough for receiving a third pin. The first angled conduit and the second angled conduit subtend a first predetermined angle. The third pin is placed through the second angled conduit of the first angled guide and into the bone. The second pin and the first angled guide are removed. The first predetermined angle is modified by disposing the third pin through a first angled conduit passing through a second angled guide. The second angled guide has a second angled conduit passing therethrough for receiving the correction pin, where the first angled conduit and the second angled conduit subtend a second predetermined angle. The first predetermined angle modified by the second predetermined angle provides the correction angle. The correction pin is placed through the second angled conduit of the second angled guide and into the bone. The third pin and the second angled guide are removed. In this way, the first predetermined angle can be modified by the second predetermined angle by addition of the second predetermined angle to the first predetermined angle to provide the correction angle. The first predetermined angle can also be modified by the second predetermined angle by subtraction of the second predetermined angle from the first predetermined angle to provide the correction angle.

With reference to FIG. 5H, an osteotomy is performed at the osteotomy site 200, where in the embodiment shown the bone 185 is cut into a first bone segment 255 including the first pin 190 and a second bone segment 260 including the correction pin 225. The first bone segment 260 and the second bone segment 265 are shown separated in FIG. 5H and rejoined in FIGS. 5I-J simply to better illustrate that the osteotomy procedure results in separation of the bone into discrete first and second segments 260, 265. As shown, the second bone segment 265 including the correction pin 225 is rotated so that the correction pin 225 and the first pin 190 are substantially parallel. However, either the first bone segment 255 or the second bone segment 260 can be rotated about the correction angle 230 so that the first pin 190 and the correction pin 225 are substantially parallel.

The first pin 190 can be held substantially parallel with the correction pin 225 using a parallel guide 270, as shown in FIG. 5I. The parallel guide 270 can be the same parallel guide 210 used previously, as shown in FIGS. 5A-C, or can be a different parallel guide 270. The parallel guide 270 has two substantially parallel conduits 275, where the first pin 190 is disposed in one conduit 275 and the correction pin 225 is disposed in the other conduit 275, as depicted in FIG. 5J. Where the parallel guide 270 is the same as the parallel guide 210 used previously, the parallel conduits 275 can correspond to the first conduit 215 and the second conduit 220.

Once the first pin 190 and the correction pin 225 are held substantially parallel, the bone 185 can be fixed across the osteotomy site 200 by various means. Bone fixation means can include various hardware components such as screws, pins, wires, and plates, as well as other means including grafts, implants, etc. The first pin 190, the correction pin 225, and the parallel guide 270 are then removed following bone fixation.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A set of guides for use in an osteotomy comprising:
a parallel guide including a first conduit passing therethrough and a second conduit passing therethrough, the first conduit and the second conduit being substantially parallel; and
an angled guide including a first angled conduit passing therethrough and a second angled conduit passing therethrough, the first angled conduit and the second angled conduit arranged at a predetermined angle, the angled guide having a substantially trapezoidal cross-section taken substantially orthogonal to a longitudinal axis, the longitudinal axis running from one parallel edge to another parallel edge of the substantially trapezoidal cross-section, the direction of the longitudinal axis defining a height of the angled guide that is greater than a length of the angled guide and that is greater than a width of the angled guide;
wherein one of the first conduit and the second conduit of the parallel guide has substantially the same diameter as one of the first angled conduit and the second angled conduit of the angled guide.

2. The set of guides of claim 1, further comprising a plurality of angled guides, each angled guide including a first angled conduit passing therethrough and a second angled conduit passing therethrough, the first angled conduit and the second angled conduit arranged at a predetermined angle, wherein the predetermined angle of each angled guide is different.

3. The set of guides of claim 2, wherein each of the predetermined angles is from about 2° to about 25°.

4. The set of guides of claim 2, wherein the plurality of angled guides includes at least two angled guides having predetermined angles selected from the group consisting of: about 2°, about 4°, about 6°, about 8°, about 10°, about 15°, about 20°, and about 25°.

5. The set of guides of claim 2, wherein each angled guide is marked with an indicia representing the predetermined angle of the respective angled guide.

6. The set of guides of claim 1, further comprising a first pin configured to fit through the first conduit of the parallel guide, a second pin configured to fit through the second conduit of the parallel guide and configured to fit through the first angled conduit of the angled guide, and a third pin configured to fit through the second angled conduit of the angled guide.

7. The set of guides of claim 1, wherein the parallel guide has a substantially rectangular cross-section taken substantially orthogonal to a longitudinal axis.

8. The set of guides of claim 1, wherein the parallel guide includes at least one orthogonal conduit passing therethrough in a direction substantially orthogonal to a longitudinal axis.

9. The set of guides of claim 1, wherein the parallel guide includes a plurality of orthogonal conduits passing therethrough in a direction substantially orthogonal to a longitudinal axis of the parallel guide, the plurality of orthogonal conduits disposed between the first conduit and the second conduit.

10. The set of guides of claim 1, wherein the angled guide includes at least one orthogonal conduit passing therethrough in a direction substantially orthogonal to the longitudinal axis.

11. The set of guides of claim 1, wherein the angled guide includes a plurality of orthogonal conduits passing therethrough in a direction substantially orthogonal to the longitudinal axis, the plurality of longitudinal conduits is disposed between the first angled conduit and the second angled conduit.

12. The set of guides of claim 1, wherein a pair of non-parallel edges of the substantially trapezoidal cross-section of the angled guide match and subtend the predetermined angle.

* * * * *